US006638307B2

(12) United States Patent
Valyunin et al.

(10) Patent No.: US 6,638,307 B2
(45) Date of Patent: Oct. 28, 2003

(54) METHODS OF SURFACE TREATMENT FOR ENHANCING THE PERFORMANCE OF A FLOATING PHAKIC REFRACTIVE LENS DESIGN

(76) Inventors: Igor Valyunin, 69 Fleurance St., Laguna Niguel, CA (US) 92607; Christopher D. Wilcox, 25161 Campina Dr., Mission Viejo, CA (US) 92690; Stephen Q. Zhou, 11 Suncreek, Irvine, CA (US) 92602

( * ) Notice: Subject to any disclaimer, the term of this patent is extended or adjusted under 35 U.S.C. 154(b) by 219 days.

(21) Appl. No.: 09/738,072

(22) Filed: Dec. 15, 2000

(65) Prior Publication Data

US 2001/0041935 A1 Nov. 15, 2001

Related U.S. Application Data

(60) Provisional application No. 60/173,894, filed on Dec. 29, 1999.

(51) Int. Cl.⁷ .................................................. A61F 2/16
(52) U.S. Cl. ..................... 623/6.56; 623/6.62; 623/912; 264/1.36; 264/1.38
(58) Field of Search ............... 623/912, 6.11, 623/6.57, 6.6, 6.62; 264/1.32, 1.36, 1.37, 1.38, 2.6

(56) References Cited

U.S. PATENT DOCUMENTS

| 4,573,998 | A |   | 3/1986  | Mazzocco ...................... 623/6 |
| 4,585,456 | A |   | 4/1986  | Blackmore ..................... 623/6 |
| 4,702,244 | A |   | 10/1987 | Mazzocco ................ 128/303 R |
| 5,147,397 | A |   | 9/1992  | Christ et al. .................... 623/6 |
| 5,192,319 | A |   | 3/1993  | Worst ............................. 623/6 |
| 5,258,025 | A |   | 11/1993 | Fedorov et al. ................. 623/6 |
| 5,300,117 | A |   | 4/1994  | Baikoff et al. .................. 623/6 |
| 5,397,848 | A |   | 3/1995  | Yang et al. .................. 525/477 |
| 5,480,428 | A |   | 1/1996  | Fedorov et al. ................. 623/6 |
| 5,584,882 | A | * | 12/1996 | Yabushita et al. .............. 623/6 |
| 5,603,774 | A |   | 2/1997  | LeBoeuf et al. ................ 134/1 |
| 5,882,421 | A | * | 3/1999  | LeBoeuf et al. ................ 134/1 |
| 6,066,172 | A | * | 5/2000  | Huo et al. ................. 623/6.56 |
| 6,399,734 | B1 | * | 6/2002  | Hodd et al. .................. 528/32 |

FOREIGN PATENT DOCUMENTS

| RU | 112032544 | 4/1989 |
| WO | 9817205   | 4/1998 |

OTHER PUBLICATIONS

"Structural Changes in IOL Surface Layer in UV–Treatment"Chabrova, C–MRS Int. Symp. Proc. 1991, vol. 3, 505–508.
Vasilets, Polymer, 39(13): 2875–2881 (1997) "Improvement of Micro–Wear Resistance of Silicone by Vacuum Ultraviolet Irradiation".

* cited by examiner

Primary Examiner—Bruce Snow
(74) Attorney, Agent, or Firm—Gardner Groff, P.C.

(57) ABSTRACT

A method of preparing phakic intraocular lenses from hydrophobic materials is described. In this process, the lens is tested to determine whether it can float submerged in an aqueous medium. If it cannot (e.g., if it remains on top of the aqueous medium), the lens is surface treated (for example, by vacuum UV or corona discharge processes) to increase its wetting ability (e.g., to reduce its hydrophobicity). The lenses prepared by this process are also described.

10 Claims, 6 Drawing Sheets

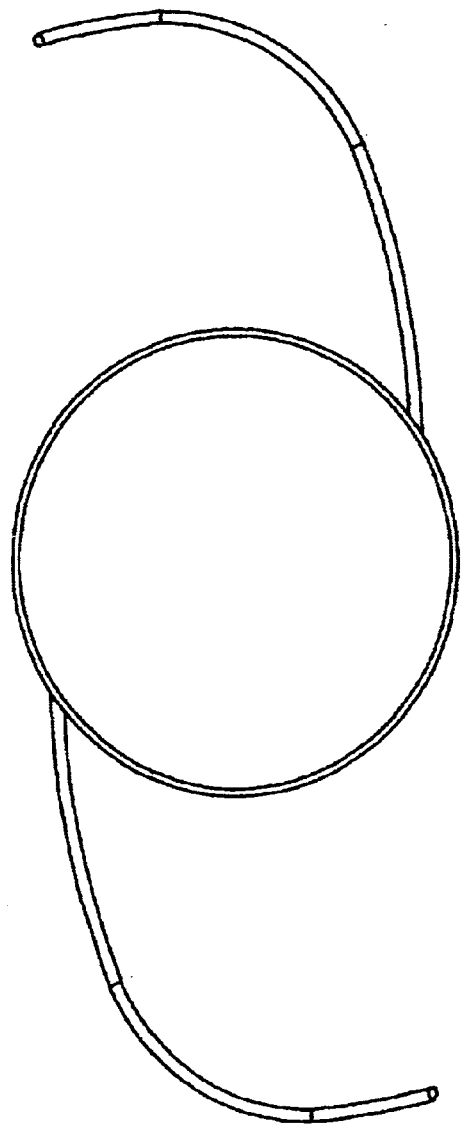
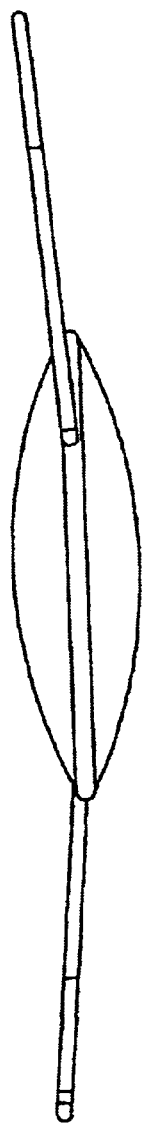
Fig. 2A                    Fig. 2B

US 6,638,307 B2

METHODS OF SURFACE TREATMENT FOR ENHANCING THE PERFORMANCE OF A FLOATING PHAKIC REFRACTIVE LENS DESIGN

This application is based on and claims priority from U.S. Provisional Patent Application No. 60/173,894, Valyunin, Wilcox and Zhou, filed Dec. 29, 1999.

BACKGROUND OF THE INVENTION

The present invention relates to intraocular lenses which are implanted in the eye to correct ametropia.

A phakic refractive lens (PRL) is surgically implanted inside the eye for correcting ametropia, particularly myopia and hyperopia. PRLs can be divided into two classes: anterior chamber PRLs and posterior chamber PRLs. An anterior chamber PRL (1) is positioned behind the cornea (2) and in front of the iris (3) while a posterior chamber PRL is behind the iris (3) and in front of the human natural crystalline lens (4) (FIG. 1). The PRL is the only reversible procedure for correcting severe refractive errors for both myopic and hyperopic patients.

There are two classes of materials that can be used for making PRLs: hydrophilic and hydrophobic materials. Although hydrophilic materials have been recently used for PRLs or intraocular lenses, their long term biocompatibility still needs to be established. On the other hand, hydrophobic materials, such as silicone and acrylic, have been used for PRLs and intraocular lenses after cataract surgery for more than a decade. These hydrophobic materials have been long established in terms of biocompatibility and are well tolerated by human eyes.

Nevertheless, when hydrophobic materials such as silicone are used to make a PRL having a floating lens design, there is a problem which needs to be solved: the silicone PRL does not submerge into an aqueous medium due to its extremely hydrophobic surface properties. The surface hydrophobicity keeps the PRL floating on the water surface instead of in water. This repelling force of the PRL from water is undesirable because the inside of the eye, whether in the anterior chamber or in the posterior chamber, is full of an aqueous liquid, i.e., the aqueous humor. The PRL needs to be surrounded with aqueous humor and its surface needs to be compatible with aqueous humor.

The present invention utilizes a number of methods that can change the PRL surface properties so that it can float submerged in an aqueous medium. Modification of the len's surface properties solves the problem of incompatibility of a hydrophobic PRL with the aqueous humor of the eye.

BACKGROUND ART

U.S. Pat. No. 4,585,456, Blackmore, issued Apr. 29, 1986, discloses a phakic intraocular lens (IOL) composed of flexible materials which is positioned against the natural lens of the eye and held in place immediately adjacent to the natural lens and the ciliary sulcus. There is no disclosure of how the phakic IOL avoids complications, such as cataract formation, or methods used for preparation of the disclosed phakic IOL.

U.S. Pat. No. 5,480,428, Federov, issued Jan. 2, 1996, discloses a novel phakic lens design which has an opening at the center of the optic body. This opening is said to allow aqueous humor to flow through the lens body, thereby preventing intra-ocular pressure (IOP) elevation, but it also reduces the optical performance of the lens. Furthermore, this patent does not disclose the method for preparation of the disclosed phakic IOL. Fedorov, in U.S. Pat. No. 5,258,025, discloses that post-operative inflammation, caused by the contact of the supporting elements of the phakic IOL with the ocular tissue, is prevented by moving supporting elements to the periphery of the phakic lens. The Zinn's zonules are thought to be strong enough to hold the supporting elements in place without causing inflammation. Thus, this patent teaches a PRL which is permanently fixed into the zonules of the eye, also called a sulcus fixation PRL. Lastly, PCT Published Application WO 98/17205, Valunin et al., published Apr. 30, 1998, describes the structure of a phakic IOL which is not fixed in the eye. Whether the disclosed lens has the ability to float submerged in water, rather than on its surface, and the surface treatment of the phakic IOL are not disclosed or discussed.

Worst, in his U.S. Pat. No. 5,192,319, issued Mar. 9, 1993, discloses an anterior chamber PRL design for correcting ametropia. No methods of preparation for such anterior chamber lenses are disclosed. Baikoff, in his U.S. Pat. No. 5,300,117, issued Apr. 5, 1994, describes another anterior chamber PRL design for correcting myopia. No methods for preparation of the lens are disclosed.

Yang, et al, in U.S. Pat. No. 5,397,848, issued Mar. 14, 1995, discloses a chemical method for enhancing the hydrophobicity of silicone polymers by introducing a hydrophilic component into the crosslinked silicone polymer networks.

Fedorov, in Russian Patent RU (11) 2032544 (1989), discloses that the use of vacuum UV in the production of ophthalmic lenses can shorten production time, and increase yields and lens biocompatibility. Specifically, lenses after application of the vacuum UV process are taught to be more resistant to the damage caused by lasers. The improvement in laser resistance is important because after cataract surgery and IOL implantation approximately 30% of the patients will develop secondary cataracts. The treatment for the secondary cataract formation utilizes a YAG laser. Therefore, IOLs need to be laser resistant. However, there is no discussion of modifying the surface energy of a PRL made from hydrophobic materials so that it can float submerged in an aqueous medium, instead of on the surface of the aqueous medium.

Vacuum ultraviolet irradiation has also been applied to silicones for improvement of micro-wear resistance (V. N. Vasilets, et al., Polymer, 39 (13): 2875–2881 (1997)). Micro-wear resistance and gamma radiation resistance are critical for equipment used in outer space exploration. Vacuum UV is one of the technologies used for improvement of surface wear. It is also known that vacuum UV will change the chemical structure, especially the surface structure of silicone materials. (See, for example, L. S. Chabrova, et al., C-MRS Int. Symp. Proc. 1991, Meeting Date 1990, Vol. 3, 505–508).

Other surface activation techniques are also well-known for various applications. For example, U.S. Pat. No. 5,147,397, Christ, issued Sep. 15, 1992, discloses the use of a plasma treatment to enhance the bondability of the haptics to the optic portion of a lens. In another example, U.S. Pat. No. 5,603,774, LeBeouf, issued Feb. 18, 1997, discloses that the tackiness associated with soft acrylic polymers can be reduced by plasma treatment of the polymer surface. In this example, plasma surface modification is used to change adhesion properties of the lens, not the hydrophilicity/hydrophobicity of the lens surface.

U.S. Pat. No. 4,573,998 (issued Mar. 4, 1986) and U.S. Pat. No. 4,702,244 (issued Oct. 27, 1987), both by Mazzocco, disclose an improved intraocular lens structure comprising a deformable optical zone portion, which enables surgeons to deform the lens, such as folding, compression, rolling, stretching, etc., so that the lens can be implanted through a smaller incision. The small incision has been shown to provide benefits to patients, such as less trauma, fast recovery and less induced astigmatism.

SUMMARY OF THE INVENTION

It is an object of the present invention to provide a PRL, with proper lens design and properties, that can be placed inside the human eye for correction of refractive errors. It is also an object of this invention that this PRL can float submerged in the aqueous humor and that the PRL be very flexible and soft. More specifically, an object of the present invention is to provide methods for modifying surface properties of a hydrophobic PRL so that it can float submerged in an aqueous medium. This capability of a hydrophobic PRL to float submerged in an aqueous medium is critical because the inside of the eye contains aqueous humor, which is an aqueous material.

These and other objects may be accomplished using a method for surface treatment of a phakic refractive lens made from hydrophobic materials (such as silicone materials) so that the treated lens can float submerged in an aqueous medium, said method comprising the steps of:

(a) testing the hydrophobic lens in an aqueous medium to ascertain whether the lens can float submerged in the aqueous medium; if the untreated lens can only float on the surface of the aqueous medium instead of floating submerged in the aqueous medium, then (b) performing a surface treatment process on the lens, such as one to make the surface of the lens more wettable (preferably less hydrophobic), for example, the vacuum UV process or the corona discharge process.

The present invention also relates to a phakic refractive lens made from a hydrophobic material which floats submerged when placed in an aqueous medium.

BRIEF DESCRIPTION OF THE DRAWINGS

FIG. 2 is a front view and a side view of a prior art anchored intraocular lens of the type used in Example 1, i.e. cataract IOLs.

DEFINITIONS

Figure 1A:
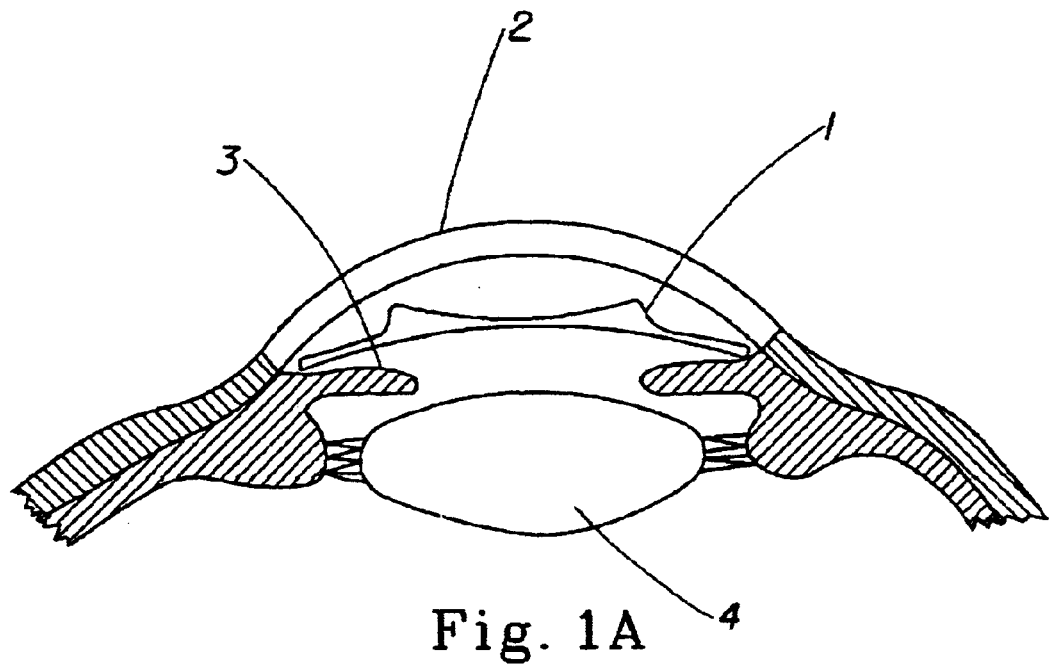
FIG. 1 is a schematic drawing showing the placement of an anterior chamber PRL and a posterior chamber PRL in the eye.
Figure 1B:
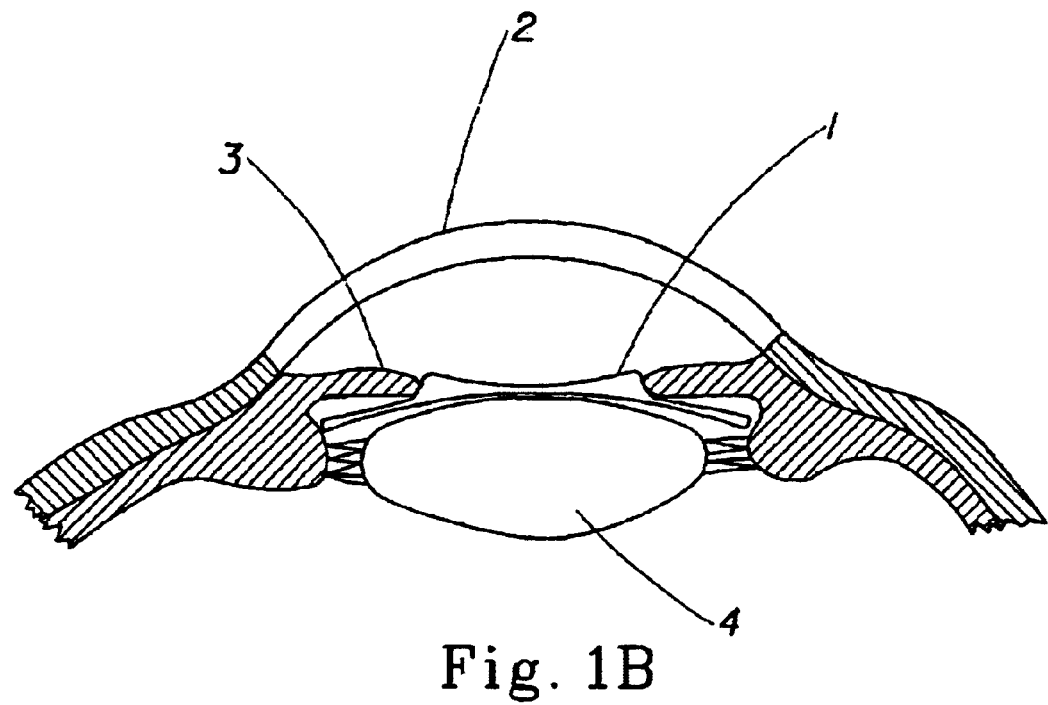

A "soft material", as used in defining the present invention, means any materials from which an intraocular lens can be made AND the resulting intraocular lens meets the requirements of a deformable optical zone portion as defined in Mazzocco's U.S. Pat. Nos. 4,573,998 and 4,702,244, i.e., the optical zone portion can be temporarily reduced in its diameter to about 80% or less of its unstressed state by means of deformation. The means of deformation include folding, compression, rolling, stretching or any combination of them.

A "foldable lens" means any lens which is made from a soft material and which can be folded or otherwise deformed without damaging its optical properties. Generally speaking, lenses made from a soft material, foldable lenses, soft lenses, foldable materials, flexible lenses, and flexible materials all include the characteristics of being deformable so that the diameter of the deformed lens is about 80% or less of its un-deformed counterpart, as defined in Mazzocco U.S. Pat. Nos. 4,573,998 and 4,702,244, incorporated herein by reference.

A "hydrophobic material" in a broad sense means that the material does not absorb or dissolve in water. Chemically speaking, hydrophobic materials do not contain a substantial amount of hydrophilic groups, such as hydroxyl (—OH), carboxylic acid (—COOH) or its anion (—COO$^-$) or ethylene oxide (—CH$_2$CH$_2$—O—). However, it may contain chemical groups such as esters (—COOR), N,N,-substituted amides (—CONRR'), etc. Typical hydrophobic material structures include long chain hydrocarbons CH$_3$—(CH$_2$)$_n$—CH$_3$, wherein n=3 or higher), fluoro-substituted hydrocarbons, and siloxane (Si—O—Si) units. In terms of its properties, a hydrophobic material is any material which has a contact angle, as measured by the Sessile drop method (air bubble in water) to be in the range of from about 60° to about 110°. For example, silicone rubber is a typical hydrophobic material with a contact angle in the range of from about 80° to about 110°. On the other hand, a typical hydrophilic material, such as poly(hydroxyethyl methacrylate), has a contact angle of about 40° or less.

"Phakic refractive lens (PRL)" generally means a lens which is surgically implanted inside the eye, either in the anterior chamber or the posterior chamber, to work together with the intact natural crystalline lens to correct refractive errors, such as myopia, hyperopia, and astigmatism. The term "PRL" generally includes both anterior chamber PRLs, and posterior chamber PRLs, unless it is otherwise specified.

"Intraocular lens (IOL)" means any lens which is surgically implanted inside the eye, either in the anterior chamber or in the posterior chamber. A "phakic intraocular lens" is the same as a "phakic refractive lens" and these terms are herein used interchangeably. An "intraocular lens for cataract surgery" (or a "cataract IOL") means a lens which is surgically implanted inside the eye to replace a diseased natural human crystalline lens, i.e. the cataract lens, after it is removed. Therefore, a cataract IOL is an aphakic lens (meaning that it is used in an eye in which the natural human lens has been removed).

An "aqueous medium" means any liquid which contains a significant portion (e.g., at least about 50% by weight) of water. The primary aqueous medium of concern here is the aqueous humor, since the lens is submersed in it in the eye. For purposes of testing herein, the aqueous medium used is deionized water (DI water). In this application, water, DI water, aqueous medium, and aqueous humor are used interchangeably.

A lens is said have "positive buoyancy" if the lens floats only on the surface of water. When it is forced into water, the lens with positive buoyancy will come back floating on the surface when the force is released. It is important that a lens be forced into the aqueous medium in order to accurately determine whether it has positive buoyancy. For example, a coin can be very carefully laid on water such that it stays on the water surface. But the coin definitely does not have positive buoyancy because when it is forced into water, it sinks down to the bottom instead of floating back to the water surface. PRLs with positive buoyancy are described in Examples 2 and 3.

A lens is said to have "neutral buoyancy" if the lens floats suspended in water. A lens with neutral buoyancy will not float on the water surface nor will it sink to the bottom of the water container. In theory, this is the ideal situation for the floating PRL design. However, it is extremely difficult to experimentally achieve neutral buoyancy.

A lens is said to have "negative buoyancy" if the lens floats in water AND gradually sinks to the bottom of the water container. It is also very important in order to determine whether a lens has negative bouyancy that, as the first step, the lens be forced into water. Then one can observe whether the lens will rise to the water surface (positive buoyancy), stay suspended in the water (neutral bouyancy), or gradually sink to the bottom of the water container (negative buoyancy) when the force is released.

It is important to note that lenses with neutral buoyancy are the most desirable for a floating PRL design, followed by negative buoyancy with a small gravity velocity (i.e., less than about 30 mm/sec, preferably about 27 mm/sec or less), then by those with a large gravity velocity. Lenses with positive buoyancy are generally undesirable for use in a floating PRL design (neutral buoyancy>negative buoyancy with a small gravity velocity>negative buoyancy with large gravity velocity). This is because inside the eye, there is an aqueous humor outflow from the posterior chamber to anterior chamber. A PRL with a small gravity velocity can easily yield to the aqueous outflow.

"Gravity velocity" is the measurement of how fast a PRL with negative buoyancy sinks to the bottom of a water container. Gravity velocity is determined by the following method. In a typical experiment, a 2000 ml graduated cylinder is filled with DI water. The height between the mark of 0 ml and 2000 ml on the graduated cylinder is approximately 434 mm. A lens is laid underneath the water surface with forceps. If visible bubbles are observed on the lens surface, they are removed with a spatula or forceps. Then, the lens is released from the forceps. The time for the lens to sink from the 2000 ml mark to the 0 ml mark on the graduated cylinder is measured and the gravity velocity is calculated. For example, for a typical silicone PRL with a −15 diopter correction, such as #7 in Table 1, it takes about 34 seconds to sink from the 2000 ml mark to the 0 ml mark on the graduated cylinder, i.e. 434 mm of distance. The gravity velocity for this PRL is said to be about 13 mm/second (434 mm divided by 34 seconds). The larger the gravity velocity, the smaller the negative buoyancy, meaning the lens sinks to the bottom of the water container faster. For comparison, the gravity velocities of PRLs and several cataract IOLs are experimentally determined and summarized in Table 1. Typically, three-piece cataract IOLs, such as Nos. 2, 3, 4 in Table 1 and shown in FIG. 2, due to their relatively large mass per surface area (about 0.3 mg/mm$^2$ or more), are not considered a floating design within the context of the present invention. In other words, three-piece cataract IOLs are considered non-floating designs, characterized by a gravity velocity of about 30 mm/second or larger.

TABLE 1

Gravity Velocities of PRLs and Other Cataract IOLs

| No. | Lens ID | Lens weight (mg) | Mass/ surface area (mg/mm$^2$) | Gravity velocity (mm/ second) | Comments |
|---|---|---|---|---|---|
| 1 | Starr plate silicone IOL[1] | 22.8 (19 Diopter) | 0.18 | 16 | Negative buoyancy |
| 2 | Allergan Si40NB[1] | 20.8 (22 Diopter) | 0.33 | 34 | Negative buoyancy |
| 3 | Pharmacia CeeOn 911[1] | 20.6 (18 Diopter) | 0.32 | 31 | Negative buoyancy |
| 4 | Alcon AcrySof[2] | 19.9 (20 Diopter) | 0.31 | 36 | Negative buoyancy |
| 5 | Silicone PRL (before UV)[3] | 10.6 | 0.08 | N/A (won't sink down) | Positive buoyancy |
| 6 | Silicone PRL (after UV)[4] | 9.8 (−8 Diopter) | 0.07 | 9 | Negative buoyancy |
| 7 | Silicone PRL (after UV)[4] | 15.6 (−15 Diopter) | 0.12 | 13 | Negative buoyancy |
| 8 | Soft acrylic PRL[5] | 15.7 | 0.12 | 27 | Negative buoyancy |

Notes:
[1] All cataract IOLs are made from silicone. They all have negative buoyancy. Starr plate has a surface area of approximately 126 mm$^2$, while other lenses have a surface area of approximately 64 mm$^2$.
[2] AcrySof is a cataract IOL made from acrylic polymer by Alcon. Its surface area is approximately 64 mm$^2$.
[3] As defined in Example 3.
[4] As defined in Example 4.
[5] As defined in Example 6.

When a lens is said to "float submerged" in an aqueous medium, it means that the lens, while submerged in water, does not float at the top surface of aqueous medium (i.e., the lens is not substantially wholly in the same plane as the top surface of the aqueous medium), but rather floats substantially completely beneath the surface of the aqueous medium. A lens, which floats substantially perpendicularly to the top surface of the aqueous medium is said to be "floating submerged" even if the top edge of the lens is at the top surface of the aqueous medium. Therefore, "float submerged" includes a lens with either neutral buoyancy or negative buoyancy.

An improvement in "wetting ability" (or wetabilty) means, in its broad sense, a decrease in buoyancy of a lens, i.e., a trend in the direction of changing from positive buoyancy to neutral buoyancy and to negative buoyancy. An improvement in wettability of a lens may be mainly due to a decrease in surface tension at the interface between the lens surface and the aqueous medium (e.g., the aqueous humor). A decrease in surface tension means less hydrophobic properties or decreased contact angle. Therefore, an improvement in wetability will lead to a decrease in buoyancy, e.g., a change from positive buoyancy to negative buoyancy. However, variables other than wetability may be a determining factor for the buoyancy of a lens, as shown in Examples 1 and 2.

A "floating PRL" design must include, among other design features, the specific properties of a PRL, whether positioned in the anterior chamber or in the posterior chamber, which floats submerged in an aqueous medium.

DETAILED DESCRIPTION OF THE INVENTION

Figure 3A:
FIG. 3 is a front view and side view of a posterior chamber PRL of the type used in Examples 2–6.
Figure 3B:
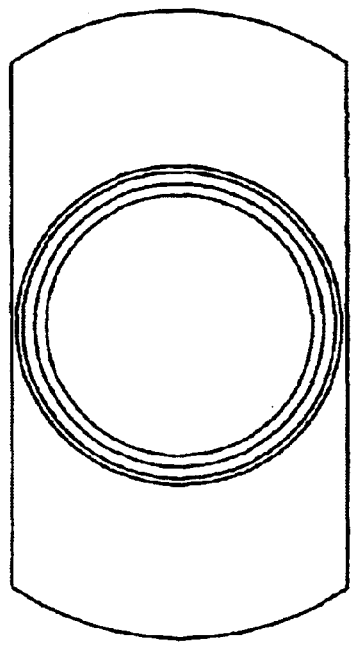

Hydrophobic materials, such as silicone and acrylic, have been used for ophthalmic implants, such as intraocular lenses for cataract surgery, for the last two decades. Their long term stability and biocompatibility have been well-established with very satisfactory results. The ability of these lenses to float is not relevant since they are generally fixed in place in the eye. An intraocular lens for cataract surgery typically has an optical diameter of 6 mm with biconvex surfaces (see FIG. 2). A cataract lens in the popular diopter range typically weighs approximately 20 mg (see Table 1). The surface area of a cataract IOL, as shown in FIG. 2, is approximately 64 mm². Because of its relatively large mass per surface area (20/64=0.31 mg/mm²), this cataract IOL cannot float on the surface when it is placed in water. It will gradually sink into water even in the case where a highly hydrophobic silicone material is used for the IOL (Example 1). In short, the hydrophobicity of a cataract IOL is not a problem for two reasons. First, the cataract lens is usually fixed inside the eye. Second, the hydrophobic cataract lens (because of its large mass per surface area) readily submerges in an aqueous medium (i.e., it has negative buoyancy, which is not the case in a PRL, see Example 2). On the other hand, a PRL (such as the one shown in FIG. 3) has a relatively large surface area. Its linear dimensions are approximately 6×11 mm, which is equivalent to a minimum surface area of about 132 mm². Typically, PRLs with configurations as shown in FIG. 3 weigh about 15 mg or less. In this case, the mass per surface area for the PRL is approximately 15/132=0.11 mg/mm². Because of this relatively small mass per surface area ratio, a hydrophobic PRL, such as one made from silicone, typically can only float on the water surface when it is placed in water. It will not penetrate the surface and float submerged in water (Example 2). In other words, a PRL made from silicone materials has positive buoyancy, a less desirable property for PRLs.

Figure 4:
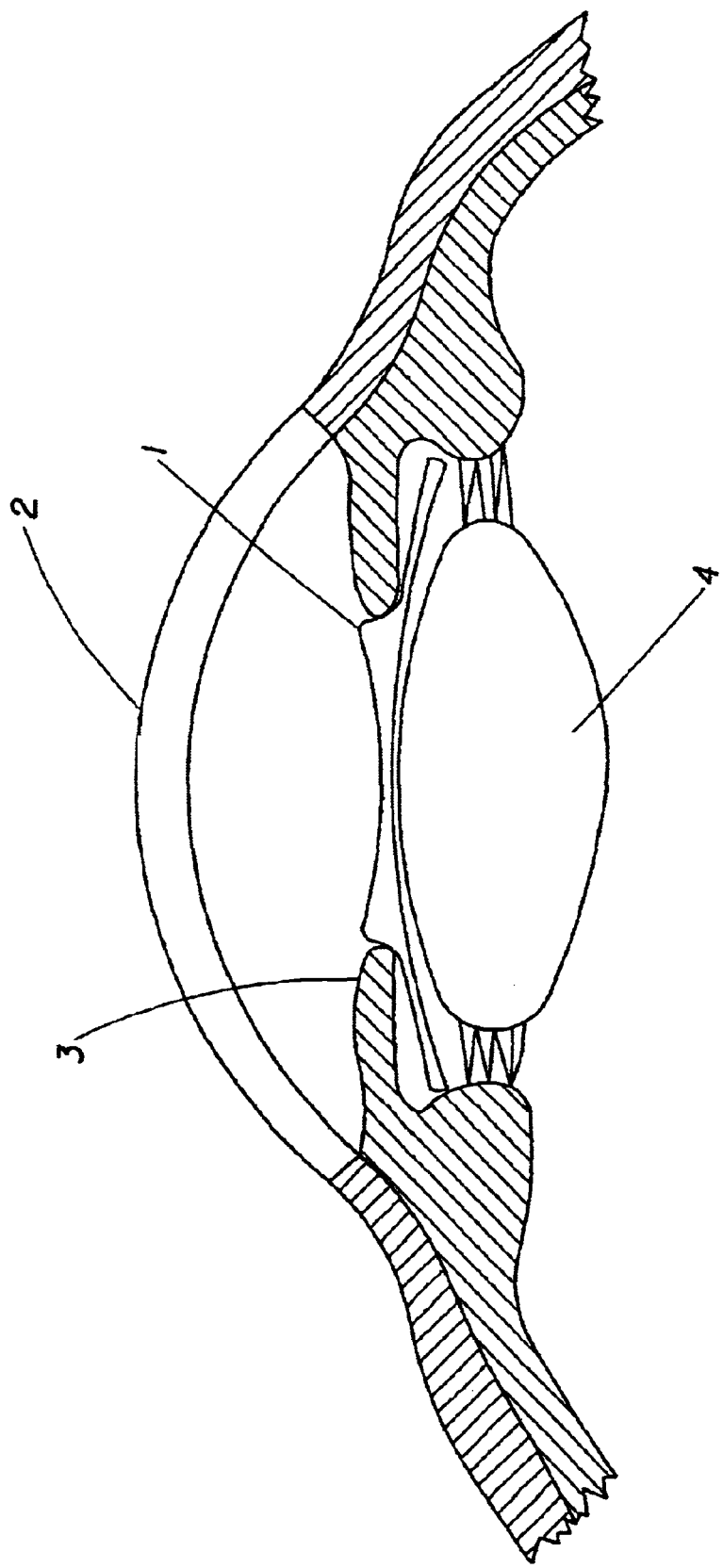
FIG. 4 is a schematic drawing showing the placement of a PRL of the present invention in the eye.

A floating posterior chamber PRL design, such as the one given in FIG. 4, has many advantages. The primary feature of the floating posterior chamber PRL design is that it does not have any permanent fixation mechanism. The posterior chamber PRL simply floats in aqueous humor. Therefore, it does not cause any permanent stress on the natural crystalline lens. Due to its floating nature, the posterior chamber PRL is constantly changing its location within the boundary determined by the haptics. When the iris contracts and moves towards the center of the anterior surface of the posterior chamber PRL, the iris may exert some pressure via the posterior chamber PRL to the natural crystalline lens. Because of its floating nature, the posterior chamber PRL does not have any localized pressure points pressing against the natural crystalline lens. This floating posterior chamber PRL simply transmits the pressure in any direction as if it were part of the aqueous medium. The stress on the natural crystalline lens caused by iris movement is dissipated by the floating posterior chamber PRL much the same way as by the aqueous humor. As a result, cataract induction by the posterior chamber PRL implantation may be minimized.

The second feature of the floating posterior chamber PRL design (FIG. 4) is that it allows the iris to move freely and constantly on its anterior surface without causing iris pigment dispersion. When the iris contracts or dilates, the posterior chamber PRL yields to the iris movement because of the floating feature and the softness of the PRL material. The iris interacts with the posterior chamber PRL as if it were part of the aqueous humor, so that iris pigment dispersion may be avoided.

The third feature of the floating posterior chamber PRL design (FIG. 4) is that it allows the aqueous humor to flow from posterior chamber to anterior chamber. In healthy eyes, this outflow occurs constantly. An ideal posterior chamber PRL should have large surface area and a small mass. This design reduces the blockage of aqueous humor resulting from placing a posterior chamber PRL in the flow path. Further, it does not require the inclusion of holes through the lens, particularly the optic surface of the lens (which can undermine the optical properties of the lens), to permit this flow to take place.

It is highly desirable that the PRL be made from a soft material. First, a soft PRL can be implanted through a smaller incision than its hard lens counterpart. Second, a soft lens is less abrasive than its hard lens counterpart. Thus, when the soft lens touches the tissue inside the eye, it will cause less potential damage to the tissue. For example, in the case of a posterior chamber PRL, the iris constantly dilates or contracts responding to the lighting conditions. When a soft material is used, the iris pigment dispersion may be minimized.

It is also true for any PRL, whether positioned in the posterior chamber or in the anterior chamber, that it be able to float submerged in water (i.e., aqueous medium). Those who are skilled in the art understand that at given conditions, PRLs made from hydrophobic materials with a small specific gravity (1.0 g/cm³ in Example 3) are preferred to ones with a larger specific gravity (1.05 g/cm³ in Example 2). A small specific gravity means a relatively low lens weight and less resistance to the outflow of aqueous humor. As a result, the floating PRL design is more effective. However, this also increases the effect of the repulsion force between the hydrophobic PRL and the aqueous medium. In other words, it increases the tendency for a hydrophobic PRL to have positive buoyancy, a less desirable property for PRLs.

There are a number of reasons why it is important for the PRL to be able to float submerged in water. First, the eye is filled with aqueous humor, an aqueous medium. The PRL, positioned either in the anterior chamber or in the posterior chamber of the eye, needs to fully submerge into the aqueous humor instead of resisting the aqueous humor due to surface tension. Furthermore, such a resistance to the aqueous humor may cause the PRL to move towards any space inside the eye which is occupied by substances less hydrophilic than the aqueous humor, such as air bubbles. Second, when the PRL is implanted into the eye, small air bubbles may collect on the PRL surface. These air bubbles exist because they act as the buffer media to bridge the extremely hydrophobic PRL surface with the extremely hydrophilic aqueous humor. These air bubbles are very hard to remove and may reduce the optical performance of the PRL. Finally, when aqueous humor flows from the posterior chamber to the anterior chamber, it may create very tiny air bubbles. These tiny individual air bubbles will accumulate and aggregate on the PRL surface.

Accordingly, the surface properties of a silicone PRL, particularly its wetting ability, need to be modified to enhance the floating design and to avoid potential complications. One important aspect of wetting ability is the hydrophobicity of the lens surface. A number of surface treatment techniques may be used for enhancing the compatibility of a silicone PRL with the surrounding aqueous humor. Examples of such techniques include the vacuum UV process and the corona discharge process. While these techniques are known, they have not heretofore been used to control the buoyancy of intraocular lens surfaces. After the surface treatment, the PRL can float submerged in water and no longer floats on the water surface. The surface treatment process enables the use of the hydrophobic materials of low specific gravity, such as 1 g/cm³ as exemplified in Example 3, for achieving the floating PRL benefits without the potential complications caused by the hydrophobic nature of the silicone material. Preferred lenses are those which weigh no more than about 15 mg., have a mass per unit surface area of no more than about 0.15 mg/mm, and which have a specific gravity at room temperature of from about 1.0 to about 1.2 g/cm$^3$, most preferably about 1.0 g cm$^3$.

Figure 5:
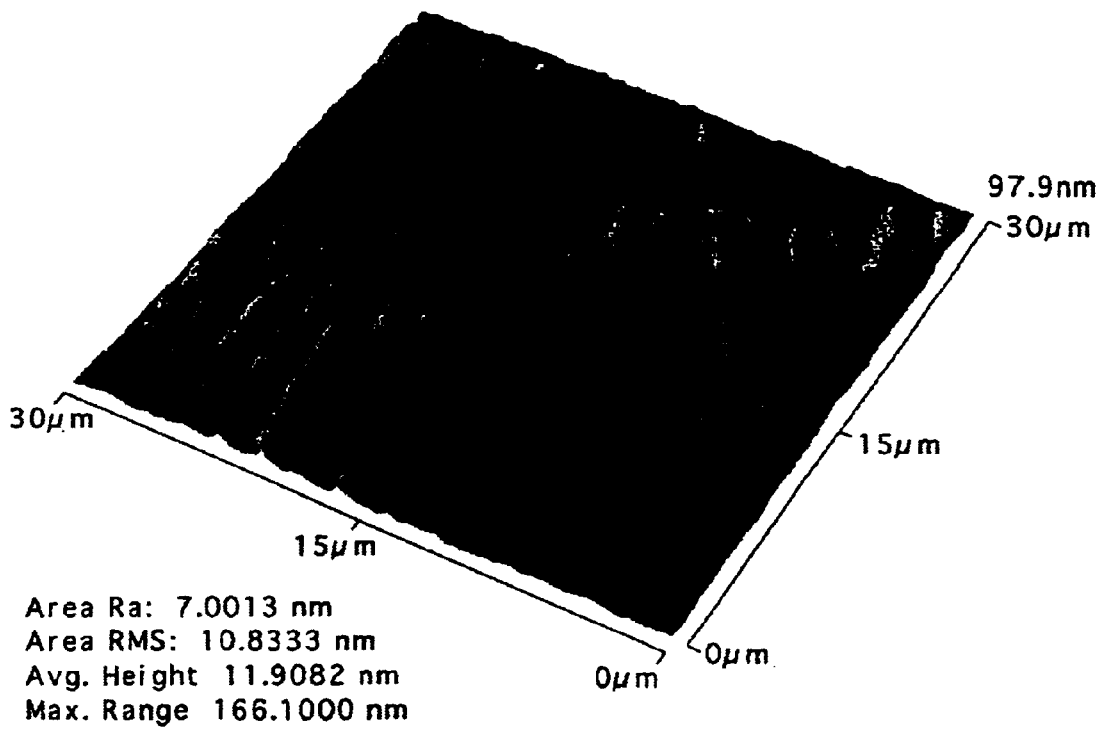
FIG. 5 is an Atomic Force Microscopy (AFM) scan of an untreated silicone PRL.
Figure 6:
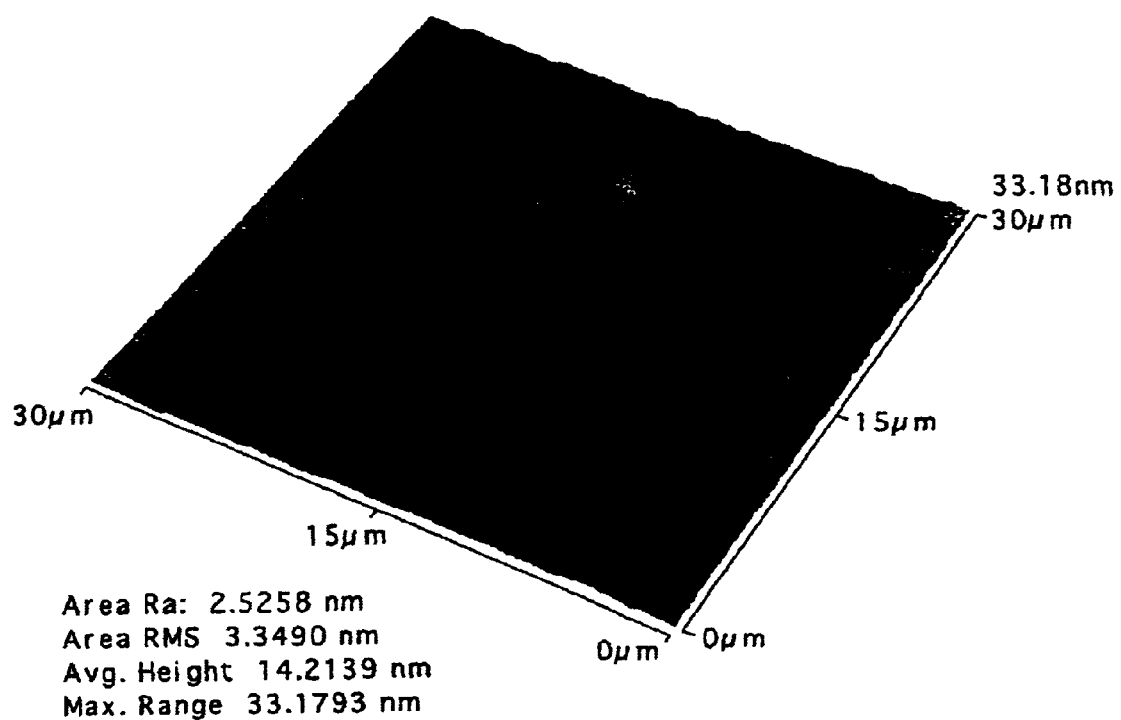
FIG. 6 is an AFM (atomic force microscopy) scan of a treated silicone PRL.

It is believed that, while other mechanisms may exist, there are at least three mechanisms by which the surface treatment processes improve the wetting ability (and therefore, the bouyancy) of the treated lenses. First, the surface treatment may increase the hydrophilicity of the untreated lens, especially when corona discharge is used as the surface treatment method. For example, an untreated silicone PRL has a contact angle of approximately 80° (see Example 3). After undergoing the corona discharge process, the contact angle changed to approximately 650 (see Example 5), an indication of a less hydrophobic surface after the surface treatment. Second, the treated lenses have an improved surface smoothness. It has been found, by means of Atomic Force Microscopy (AFM), that the treated lens surface is smoother than its untreated counterpart. For example, FIG. 5 shows an untreated silicone PRL. Its roughness, as described by Area Ra, is 7.9 nm for the untreated lens and decreases to 2.5 nm for the treated lens (FIG. 6). In a typical experiment, the area Ra of an untreated PRL is in the range of approximately 7–9 nm while a treated PRL is in the range of 2–6 nm. Ra is the arithmetic mean roughness of a surface (i.e., the arithmetic mean of the absolute deviations from the mean surface level). The larger the Ra, the rougher the surface. A smoother surface means a smaller effective surface area, which in turn means a smaller expulsion force between the lens surface and the aqueous media. Third, the treated surface frequently has a higher crosslinking density, as evidenced by the ESCA experiment. ESCA stands for Electron Spectroscopy for Chemical Analysis, and is also known as X-ray Photoelectron Spectroscopy, or XPS. In a typical ESCA experiment, C % was decreased from about 61% for an untreated lens to about 58% for a treated PRL, while O% increased from about 18.5% to about 21%. This indicates a higher crosslinked surface by the formation of additional silicon-oxygen (Si—O) bonds caused by the surface treatment. This higher crosslinking density yields a higher gravity density of the lens surface, which in turn helps the lens to float submerged.

In addition, the following observations regarding contact angle changes further support that the surface dynamics of a PRL have been modified by the vacuum UV process. The Sessile Drop Method (water drop in air) was used to measure the contact angle with a Rame-Hart Goniometer. In one experiment, a non-UV treated lens has the initial contact angle of approximately 92% (i.e., at time zero) and gradually changes to about 84° in about 5 minutes. On the other hand, a UV treated lens has changed its contact angle from approximately 89° at time zero to 650 in about 5 minutes. This enhanced responsiveness of the surface microstructure change when exposed to the aqueous environment of a UV treated lens is consistent with the composition change found by ESCA. In other words, the increased amount of Si—O bonding after the UV process has accelerated the lens surface to rearrange itself to lower the contact angle because a Si—O bond can form a hydrogen bond with water molecules. An increased amount of Si—O bonding at the lens surface means an increased interaction between the PRL and the aqueous medium, therefore, a more compatible surface than its non-UV treated counterpart.

To summarize, the key to lenses of the present invention is that they float submerged in an aqueous solution (i.e., they have neutral or negative bouyancy). Preferred lenses are those having a gravity velocity of about 27 mm/second or less in an aqueous medium. There are numerous factors which can affect a lens' property of being able to float submerged, for example, its hydrophobicity, weight per surface area, or specific gravity. Any of these factors can be adjusted, as long as the final lens floats submerged in an aqueous medium. Preferred lenses are those which have any or all of the following properties: specific gravity of from about 1.0 to about 1.2 g/cm$^3$ at room temperature, a weight of no more than about 16 mg, a mass per surface area of no more than about 0.15 mg/mm$^2$, or a contact angle of from about 60° to about 110°. Even if a particular lens, when constructed, is unable to float submerged, surface treatment of that lens (for example, using the UV or corona discharge methods, described above) may enable it to float submerged.

EXAMPLES

The following examples are given for the purpose of illustrating the present invention.

Contact angle is a measurement of surface hydrophobicity (or hydrophilicity). In the present application, the Sessile Drop Method and a Rame-Hart Goniometer were used for the measurement. In a typical test, the average of 12 readings was used for reporting purposes. A typical hydrophobic material, such as silicone, has a contact angle in the range of about 80° or higher, while a typical hydrophilic material, such as poly-HEMA, has a contact angle in the range of about 40° or lower.

Example 1

Silicone Cataract Intraocular Lens (IOL) with Negative Buoyancy

An intraocular lens for cataract surgery was made from a hydrophobic silicone material, Med 6820 supplied by NuSil Silicone Technology. This cataract IOL has a shape and dimensions illustrated in FIG. 2.

The cataract IOL was placed in DI water and it was observed that the cataract IOL does not float on the water surface; it sinks to the bottom of the container. It requires a much larger force to disturb the water in order to let the IOL temporarily float in water. This is because the mass of this cataract lens is much larger than the floating force. In this case, the surface area of the cataract IOL is approximately 64 mm$^2$. The cataract IOL weighs 20 mg. Therefore, the mass per unit surface area for this cataract IOL is approximately 0.31 mg/mm$^2$, causing the lens to have negative buoyancy.

Other physical and mechanical properties of the Med 6820 silicone material are as follows: tensile strength 750 psi; elongation 125%; refractive index: 1.43; specific gravity: 1.05 g/cm$^3$ at room temperature. The specific gravity measurement is based on ASTM D792 Specific Gravity and Density of Plastics by Displacement, using a Cahn DCA312 Dynamic Contact Angle Analyzer. The contact angle as measured by Sessile Drop Method (air bubble in water), using a Rame-Hart Goniometer is 95°. The hardness is in the range of 40 to 50 Shore A.

Example 2

Silicone PRL Floating on Water Surface (i.e. Positive Buoyancy)

The same hydrophobic silicone material as in Example 1 was used to prepare PRLs under the following conditions. Equal amounts of Part A and Part B of the silicone material were mixed for 10 minutes. The mixture was transferred to a syringe and degassed under vacuum until all the visible air bubbles disappeared. A very small amount of the mixture was poured into a metal alloy mold and cured at 120° C. for 70 minutes. The PRL was removed from the mold and placed in DI water with the posterior side facing down. The PRL was observed to float on the water surface. When a spatula or forceps was used to gently push the PRL into the water, the PRL rises back onto the water surface as soon as the spatula is removed from the PRL, indicating a positive buoyancy. Since the silicone material used in both Examples 1 and 2 is the same, the lenses therefore having the same surface properties, it is the mass per surface area, which determines whether the lens has negative or positive buoyancy in this case.

The PRL has a configuration and dimensions as shown in FIG. 3. The physical and mechanical properties of the hydrophobic PRL material are same as in Example 1.

Example 3

Another Silicone PRL Floating on Water Surface (Positive Buoyancy)

SIEL 1.46 is a hydrophobic silicone material (commercially available from SILL, Ltd., Moscow) with a refractive index of 1.46 and specific gravity of 1 g/cm$^3$. Ten parts of Part A and one part of Part B of the silicone material were mixed for 5 minutes. The mixture was transferred to a sealed vial and stored in a freezer overnight. A small amount of the mixture (about 30 mg or less) was placed onto a metal mold. The material was cured in a pre-heated oven at 120° C. for 70 minutes. The PRL has a configuration and dimensions as shown in FIG. 3.

The PRL was placed in deionized water and was observed to float on the water surface. A spatula or forceps was used to gently push the PRL into the water. As soon as the pushing force was released, the PRL floated back onto the water surface. Even when the whole PRL was pulled into water, it came back on the water surface as soon as the pulling force was released, indicating that the PRL has positive buoyancy. The contact angle (air bubble in water) of the PRL was 80°. The Shore A hardness of the PRL material was in the range of 20 to 25.

PRLs with configurations shown in FIG. 3 typically weigh about 15 mg or less in the most commonly used diopter range (−3 to −14 D). The surface area of the PRL 2 is approximately 132 mm. Therefore, the mass per unit surface area is approximately 0.11 mg/mm$^2$ or less.

The hydrophobic silicone used in Example 3 has a specific gravity of 1 g/cm$^3$, essentially the same as that of water. Those who are skilled in the art understand that a PRL made from this hydrophobic silicone PRL does not immerse itself in water. Unless the PRL surface becomes compatible with water, it will indefinitely float on water surface. Example 4 below illustrates how the PRL surface changes to become compatible after a surface treatment process.

Example 4

Silicone PRL Floating Submerged in Water after Vacuum UV Process (Negative Buoyancy)

PRLs prepared in Example 3 can be treated by a vacuum ultraviolet process as follows: Ten PRLs were placed into a fixture mounted inside a vacuum chamber. When the pressure inside the vacuum chamber was reduced to the range of 2–7 mm-Hg, the UV lamp (Hamamatsu, Type L 879) was ignited. PRLs were exposed to the UV light for 5–25 minutes. This procedure was repeated for the unexposed side of each PRL. A narrow-band filter is preferably used between the UV light source and the PRLs. The wavelength of the vacuum UV was in the range of 115 to 200 nm.

The treated PRL was placed on and was gently pushed into deionized water with a spatula or forceps. It was observed that it floated submerged in water. Without the turbulence, the PRL will gradually settle down to the bottom of the container with a gravity velocity of about 15 mm/second or less, depending on the diopter of the PRL (see Table 1, example Nos. 6 and 7). However, when there is a small turbulence, the treated PRL floats temporarily in water again. In fact, the treated PRL cannot float on the surface of deionized water as the untreated PRL does. In conclusion, the surface treatment has changed the PRL from a positive buoyancy to negative buoyancy.

Example 5

Silicone PRL Floating Submerged in Water after Corona Discharge Process (Negative Buoyancy)

PRLs prepared in Example 3 can be alternatively treated by corona discharge as follows: Two PRLs were placed on the rack (Model T P/N 2602-015, by Emerson Electric Co.) where the PRLs are about half an inch away from the corona discharge. The corona discharge (Model BD-20, 115 volts, 50/60 Hz, 0.35A power supply by Electro-Technic Products, Inc.) was turned on. The PRLs on the moving rack passed through the corona discharge 10 times (one minute per pass). The same procedure was repeated on the unexposed side of the PRLs.

The treated PRL was placed in deionized water. It was observed that the treated PRL did not remain on the water surface. Rather, the treated PRL floats submerged in water. Without the turbulence, the PRL will gradually settle down to the bottom of the container (gravity velocity<27 mm/sec). However, when there is a small turbulence, the treated PRL floats temporarily in water again. Contact angle measurement indicated that the treated PRL has a contact angle of 65°. Therefore, the corona discharge changed the PRL from positive buoyancy to negative buoyancy. It also lowered the contact angle of the PRL surface, an indication of less hydrophobic surface after the treatment.

Example 6

Acrylic PRL

A mixture of 48 grams of ethylene glycol phenyl ether acrylate, 2 grams of bisphenol A propoxylate diacrylate, 0.65 grams of 2-(4-benzoyl-3-hydroxyphenoxy) ethyl acrylate, and 50 milligrams of azobisisobutyronitrile was deaired with ultra-pure nitrogen gas for about 15 minutes. This mixture can be used for making the PRL directly or can be pre-gelled with the pre-gelled mixture being transferred into a mold. Curing conditions are: temperature 90–110° C.; time 11–16 hours. Other properties of this acrylic material are: refractive index: 1.558; glass transition temperature: 7° C.; lens weight: 15.7 mg' Shore A hardness: 36; tensile strength/elongation %: 280 psi/160%. The specific gravity of this material is 1.21 gram/cm$^3$. The contact angle of this polymer is 81°. The lens has a configuration and dimensions shown in FIG. 3.

When this PRL was placed in deionized water with the posterior side facing down, it floats on the water surface. The PRL can be forced into the water and can float beneath the surface of the water when it is slightly disturbed. In other words, this soft acrylic PRL readily floats submerged in water, probably due to the fact of a high specific gravity (1.21 gram/cm$^3$) and lower hydrophobicity than a typical silicone. This high specific gravity is also the reason for the relatively large gravity velocity (27 mm/second) of this acrylic PRL.

After this acrylic PRL was treated with vacuum UV in the same way as that in Example 4, it was observed that the treated PRL can easily float submerged in an aqueous medium.

We claim:

1. A method for surface treatment of a phakic refractive lens (PRL) made from hydrophobic materials so that the treated PRL can float submerged in an aqueous medium, said method comprising the steps of:
   (a) testing the hydrophobic PRL in an aqueous medium to ascertain whether the PRL can float submerged in the aqueous medium; if the untreated PRL can only float on the surface of the aqueous medium instead of float submerged in the aqueous medium, then
   (b) performing a surface treatment process on the untreated PRL.

2. The method according to claim 1 wherein the surface treatment process makes the surface of the PRL less hydrophobic.

3. The method according to claim 1 wherein the surface treatment process increases the wetting ability of the surface of the PRL.

4. The method according to claim 1 wherein the surface treatment process is selected from the vacuum UV process and the corona discharge process.

5. The method according to claim 1 wherein the lens is made from materials selected from silicone materials and acrylic materials.

6. A method of manufacturing a phakic refractive lens comprising the steps of:
   (a) providing a lens structurally adapted to float in the posterior chamber of the eye, made from a soft hydrophobic material, said lens having a positive buoyancy; and
   (b) treating the surface of said lens thereby providing said lens with a negative buoyancy as measured by a gravity velocity of about 27 mm/sec. or less in an aqueous medium.

7. The method according to claim 6 wherein said lens comprises an optical body and a plurality of haptic bodies attached to and extending outwardly from said optical body.

8. The method according to claim 6 wherein said lens has no permanent fixation in the eye and is structurally adapted to float between the iris and the anterior surface of the natural lens capsular bag when positioned in the posterior chamber of the eye.

9. The method according to claim 6 wherein said hydrophobic material is selected from silicone and soft acrylic materials.

10. The method according to claim 6 wherein the surface of said lens is treated by a process selected from the vacuum UV process and the corona discharge process.

* * * * *